US006207109B1

(12) United States Patent
Richard et al.

(10) Patent No.: US 6,207,109 B1
(45) Date of Patent: Mar. 27, 2001

(54) STERILANT GAS MIXTURES OF PENTAFLUORODIMETHYL ETHER AND ETHYLENE OXIDE

(75) Inventors: Robert Richard, Cheektowaga; James Batt, Depew; Barbara Decaire, West Amherst; Ian Shankland, Williamsville, all of NY (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 08/329,346

(22) Filed: Oct. 26, 1994

(51) Int. Cl.$^7$ ................. A01N 1/00; A01N 3/00
(52) U.S. Cl. .............. 422/34; 422/37; 252/372; 252/601; 252/605
(58) Field of Search ............ 422/34, 37; 252/372, 252/601, 605; 424/45

(56) References Cited

U.S. PATENT DOCUMENTS

| | | | |
|---|---|---|---|
| 3,068,064 | * | 12/1962 | McDonald . |
| 3,589,861 | * | 6/1971 | Gunther . |
| 4,130,393 | * | 12/1978 | Fox ............................... 422/34 |
| 4,775,679 | * | 10/1988 | Chang et al. ................. 514/397 |
| 4,948,526 | * | 8/1990 | Fellows et al. ................. 252/69 |
| 4,954,284 | | 9/1990 | Batt et al. .................... 252/170 |
| 4,971,716 | | 11/1990 | Batt et al. .................... 252/171 |
| 4,976,922 | * | 12/1990 | Chippett et al. ............... 422/34 |
| 5,039,485 | | 8/1991 | Conviser et al. ............... 422/34 |
| 5,254,280 | * | 10/1993 | Thomas et al. ................. 252/68 |
| 5,254,309 | | 10/1993 | Felix et al. .................... 422/34 |
| 5,314,682 | | 5/1994 | Sweval et al. .................. 424/45 |
| 5,342,579 | | 8/1994 | Conviser et al. .............. 514/475 |
| 5,346,669 | | 9/1994 | Sweval et al. ................. 422/34 |
| 5,376,333 | * | 12/1994 | Shankland et al. ............. 422/34 |

FOREIGN PATENT DOCUMENTS

9402564 * 3/1994 (WO).

OTHER PUBLICATIONS

"Physical Property Data on Fluorinated Propanes and Butanes as CFC & HCFC Alternatives", Beyerlein et al EPA report; 121 3–5191.*

* cited by examiner

*Primary Examiner*—Nina Bhat
(74) *Attorney, Agent, or Firm*—Colleen D. Szuch; Marie Collazo

(57) ABSTRACT

The invention is directed to sterilant gas compositions of pentafluorodimethyl ether and ethylene oxide which possess improved environmental properties.

20 Claims, No Drawings

STERILANT GAS MIXTURES OF PENTAFLUORODIMETHYL ETHER AND ETHYLENE OXIDE

BACKGROUND OF THE INVENTION

This invention relates to novel compositions comprising ethylene oxide and pentafluorodimethyl ether which possess improved environmental and nonflammability characteristics. These compositions are useful in the gaseous sterilization of heat and/or moisture sensitive materials.

Sterilization with a germicidal agent, such as ethylene oxide gas or ethylene oxide containing gas mixtures, has played an increasingly important role in sterilizing heat or moisture sensitive materials. Rapid growth in the use of sterile, disposable medical devices is just one consequence of gaseous sterilization with agents such as ethylene oxide. Gaseous sterilization of reusable medical and surgical equipment using a nonflammable mixture of ethylene oxide and a carrier gas has also proven to be reliable, cost effective technology for many hospitals.

The basic gaseous sterilization process consists of evacuating the sterilization chamber containing the articles to be sterilized, preconditioning the articles at an optimal relative humidity, generally between 20–70% relative humidity, admitting the sterilizing gas at an appropriate pressure and temperature, maintaining contact between the sterilizing atmosphere and the articles to be sterilized for an appropriate time, and finally discharging and evacuating the chamber to remove the sterilant gas.

Although there are many variations on the basic process, the major factors which have to be controlled in order to effect the sterilization are exposure time, temperature, ethylene oxide pressure or partial pressure, and relative humidity. The following prior art references provide a good description of the standard sterilization processes and apparatus with which the gaseous sterilizing agents of the invention are useful: J. J. Perkins, *Principles and Methods of Sterilization* 2nd. Ed. 501–530 (1969) and "Ethylene Oxide Gaseous Sterilization For Industrial Applications" *Industrial Sterilization International Symposium*, 181–208 (1972), U.S. Pat. No. 3,068,064 and U.S. Pat. No. 3,589,861.

By itself, ethylene oxide is an extremely flammable gas. Its flammability range extends from about 3.0% by volume to 100% by volume in air. Thus, when ethylene oxide is used alone as a sterilizing gas, precautions such as explosion proof equipment are mandatory.

A preferable practice is to blend the ethylene oxide with another fluid which serves to dilute the ethylene oxide and render the mixture as a whole, nonflammable. Two such blends which have been used as sterilizing gases are dichlorodifluoromethane (chlorofluorocarbon (CFC)-12)/ethylene oxide and carbon dioxide/ethylene oxide. Inert carrier gases like CFC-12 and carbon dioxide inhibit the flammability of ethylene oxide and provide sufficient autogeneous pressure to deliver the liquid mixture from the source cylinder to the heat exchanger of the sterilizer vessel where the liquid mixture is vaporized.

The CFC-12/ethylene oxide blend is generally supplied as a liquid mixture consisting of 88% by weight CFC-12 and 12% by weight ethylene oxide. This composition is below the critical flammability composition of about 14–15% by weight ethylene oxide in CFC-12, and is therefore nonflammable. A typical hospital sterilization process which utilizes the CFC-12/ethylene oxide blend is performed by evacuating the chamber to about 20–24 inches of mercury vacuum, preconditioning the articles at an optimal relative humidity, and filling the chamber to about 10 psig pressure with the gas mixture. Sterilization is generally performed around 130° F. The 88/12 by weight CFC-12/ethylene oxide mixture produces a gas mixture containing 72.8 volume or mole percent CFC-12 and 27.2 volume or mole percent ethylene oxide. This composition provides about 630 milligrams of ethylene oxide per liter at the stated typical operating condition. The concentration (mg/liter) of ethylene oxide present in the sterilization chamber is critical in determining the required exposure time and ultimate sterilization efficiency. The Association for the Advancement of Medical Instrumentation (AAMI) recommends a minimum ethylene oxide concentration of 400 mg/liter.

The nonflammable carbon dioxide/ethylene oxide blend is also supplied as a liquid mixture consisting of about 90% by weight carbon dioxide and about 10% by weight ethylene oxide. This blend produces a gas mixture containing 90% by volume or mole carbon dioxide and 10% by volume or mole ethylene oxide. The available ethylene oxide concentration (mole percent) is significantly less than that obtained from the 88/12 by weight CFC-12/ethylene oxide blend. Sterilization using carbon dioxide/ethylene oxide is generally performed at a greater pressure than that used with CFC-12/ethylene oxide to increase the concentration of ethylene oxide, or is performed for greater exposure times which decreases productivity.

Although the major purpose of the inert carrier gas component in these sterilizing gas mixtures is to mask the flammability characteristics of ethylene oxide, simple substitution of an arbitrary nonflammable gas does not necessarily ensure a useful sterilizing gas mixture. First, the flammability properties of the blend must be such that sufficient ethylene oxide (mg/liter at a typical pressure and temperature) is delivered by the blend to effect the sterilization in an appropriate time. If the carrier gas does not mask the flammability to a sufficient extent, a lower concentration of ethylene oxide must be used to ensure nonflammability. In such cases, either a longer exposure time is required to perform the sterilization, which affects productivity, or greater operating pressures are required to increase the effective ethylene oxide density in the sterilization chamber. Increasing the operating pressure is generally not a viable option because existing sterilization chambers may not be rated for the increased pressure, and as pointed out by Gunther in U.S. Pat. No. 3,589,861, increased pressure can lead to swelling and rupture of the sealed plastic bags commonly used to package disposable medical devices. Indeed, lower operating pressures are advantageous in this respect. The requirement for a greater operating pressure or increased exposure time has limited the acceptance of the 90/10 carbon dioxide/ethylene oxide mixture in comparison to the 88/12 CFC-12/ethylene oxide mixture.

A candidate inert diluent or carrier gas must also be miscible with ethylene oxide in the liquid phase and must not segregate from the ethylene oxide to any great extent during vaporization. Segregation or fractionation can lead to potentially flammable or explosive situations. The degree of segregation that may occur during evaporation is related to the relative volatility of the components of the mixture. The vapor pressure of ethylene oxide at 70° F. is 22 psia while the vapor pressures of CFC-12 and carbon dioxide at 70° F. are 85 and 850 psia, respectively. The vapor pressure data indicate a very large difference in volatility between carbon dioxide and ethylene oxide and, hence, a susceptibility for carbon dioxide/ethylene oxide blends to fractionate.

Because CFC's like the fully halogenated CFC-12 have been implicated in causing environmental problems such as stratospheric ozone depletion and global warming they are not preferred diluents. The trend in the industry is toward the use of stratospherically safer (i.e. hydrogen containing) materials as the flame suppressing diluent. Hydrochlorofluorocarbon (HCFC)-based diluents such as 1-chloro-1,2,2, 2-tetrafluoroethane (HCFC-124) and a blend of chlorodifluoromethane (HCFC-22)/HCFC-124 are currently being used. These materials are available from AlliedSignal Inc. of Morristown, N.J. Even though these materials possess significant environmental advantages over perhalogens (lower ozone depletion potentials), because they contain some chlorine they are viewed as temporary solutions with limited lives.

Materials such as the hydrofluorocarbons or HFC's, which contain fluorine, hydrogen and no chlorine, are more acceptable. Examples of these materials are HFC-125 and HFC-227. They have zero or essentially zero ozone depletion potentials and atmospheric lifetimes of substantially less than the CFC's. Other materials that contain fluorine, hydrogen but no chlorine such as ethers are also candidate diluents. Pentafluorodimethyl ether is one such compound. It is essentially non-ozone depleting and has an atmospheric lifetime of about 17 years, which is significantly lower than that of most CFC's (CFC-12/116 year lifetime)

DESCRIPTION OF THE INVENTION

This invention is directed to novel compositions of ethylene oxide and pentafluorodimethyl ether (HFE-125) which are nonflammable, compatible with objects being sterilized; chemically stable; environmentally acceptable; minimally segregating; deliver at least 400 mg/liter (AAMI command practice) of ethylene oxide to the sterilization chamber; and provide sufficient vapor pressure to deliver the liquid mixture to the sterilization chamber.

HFE-125 is commercially available from PCR Inc. of Gainesville, Fla. Alternatively, it may be prepared by following the syntheses disclosed in Chem. Abstracts 55.23312b, 55.27012i and 55.27013a. Other methods for the manufacture of HFE-125 will readily occur to those skilled in the art.

The DOT § 173.115 classifies a flammable gas as one that has a lower flame limit less than or equal to 13 vol % in air or has a flammable range of greater than or equal to 12 vol % in air. This allows a mixture that has high narrow flame limits to be labeled and transported as a nonflammable gas. Using this definition, in order to be classified as nonflammable, the allowable amount of ethylene oxide in HFE-125 is 26.7 mol %.

The nonflammable pentafluorodimethyl ether/ethylene oxide compositions of the invention comprise effective amounts of a flame suppressing composition comprising pentafluorodimethyl ether and ethylene oxide.

The primary function of the ethylene oxide component of the invention is to facilitate sterilization while the primary function of flame suppressing composition comprising pentafluorodimethyl ether is to mask the flammability of the ethylene oxide. Thus, when these components are combined in effective amounts an efficient, nonflammable sterilizing gas composition results.

The preferred embodiments of the invention are listed below:

Sterilizing gas compositions comprising from about 6.5 to about 27 mole percent ethylene oxide and from about 93.5 to about 73 mole percent of a flame suppressing composition comprising pentafluorodimethyl ether.

A more preferred sterilizing gas composition comprises from about 17.2 to about 21.8 mole percent ethylene oxide and from about 82.8 to about 78.2 mole percent of a flame suppressing composition comprising pentafluorodimethyl ether.

The most preferred sterilizing gas composition comprises about 17.3 mole percent ethylene oxide and about 82.7 mole percent of a flame suppressing composition comprising pentafluorodimethyl ether.

The handling and delivery of sterilant gas compositions differs depending on the application and site. In certain applications, for example, it may be desirable to increase or decrease the autogeneous pressure of the sterilant composition. This can be accomplished by incorporating another component into sterilant composition. Suitable third components are those which are nonflammable, more volatile (or less volatile depending on application/site) than the sterilant composition (i.e., HFE-125/EO); inert; and capable of dissolving in the sterilant blend. Where increasing the autogeneous pressure is the aim, such materials include carbon dioxide, pentafluoroethane (R-125), trifluoromethane (R-23), carbon tetrafluoride (R-14), and hexafluoroethane (R-116). Where one would like to decrease the autogeneous pressure of the sterilant composition such materials include heptafluoropropane (R-227ea and 227ca), octafluorocyclobutane (C-318), propylene oxide and tetrafluoroethane (R-134 and R-134a).

When a third component is present, it is generally present in an amount of from about 1 to about 92.5 mole percent of the sterilant composition.

Thus, in another embodiment, the invention comprises a sterilizing gas composition of from about 6.5 to about 27 mole percent ethylene oxide, from about 92.5 to about 1 mole percent of a flame suppressing composition comprising pentafluorodimethyl ether and from about 1 to about 92.5 mole percent of a non flammable, inert component which is more volatile than the pentafluorodimethyl ether/ethylene oxide blend and is capable of increasing the autogeneous pressure of the blend.

Another technique which may be used to increase the pressure of the sterilant composition is to pressurize the head space of the cylinder from which the sterilant composition is expelled with an inert gas such as $SF_6$, He, and $N_2$. This technique may also be used to increase flow rate or delivery height of the sterilant composition. When an inert gas is used, typically it is present in an amount sufficient to increase the pressure of the sterilant composition in an amount of from about 1 to about 150 psi.

Thus, in another embodiment, the invention is directed to a process for increasing the pressure, flow rate or delivery height of the sterilant composition comprising adding to the headspace of the container which houses the sterilant composition an effective amount of an inert gas.

In still another embodiment, the invention comprises a sterilizing gas composition of from about 6.5 to about 27 mole percent ethylene oxide, from about 92.5 to about 1 mole percent of a flame suppressing composition comprising pentafluorodimethyl ether and from about 1 to about 92.5 mole percent of a non flammable, inert component which is less volatile than the pentafluorodimethyl ether/ethylene oxide blend and is capable of decreasing the autogeneous pressure of the blend.

In the process embodiment of the invention, the compositions of the invention may be used as sterilizing gases in any manner well known in the art. Generally, the sterilizing process comprises exposing the articles to be sterilized to the sterilizing gas composition under conditions and for a period of time necessary to achieve the desired degree of sterility.

Typically, the process is effected by placing the articles to be sterilized in a chamber, evacuating and humidifying the chamber, and exposing the articles to the sterilizing gas composition for an appropriate period of time.

Ethylene oxide has a flash point of less than −20° F., and forms explosive mixtures in air from about 3.0 volume percent to 100 volume percent ethylene oxide. The addition of a chemically inert vapor or gas decreases the flammability of the ethylene oxide/air mixture. With sufficient inert component the blend is rendered nonflammable. If the inert component is truly inert, that is, it does not participate chemically in the combustion process, then the extinction efficiency of the inert species depends on such physical properties as its specific heat and thermal conductivity. See, for example, H. F. Coward and G. W. Jones, *Limits of Flammability of Gases and Vapors*, Bulletin 503, 5 (1952). The physical extinction mechanism relies upon removal of the energy required to maintain combustion.

The flammability properties of ethylene oxide/halocarbon blends do not follow this simple physical correlation (as shown in the Examples). Rather, it is well known their extinction properties stem from a chemical mechanism whereby the halogen species chemically participates in the combustion reaction, interfering with or inhibiting the combustion reaction. R. Hirst in *Institution of Fire Engineers Quarterly*, Vol. 25, No. 59, 231–250 (1965) states that the extinguishing ability of halogen species follows the order I>Br>Cl>F. Iodine containing halocarbons are generally known to be less chemically stable and more toxic than other members of the halocarbon family. The bromine containing species are known to possess a much greater ozone depletion potential than their chlorine containing analogs. Thus, for environmental reasons, potential halocarbon carrier gases are restricted to the hydrohalocarbons containing fluorine and/or chlorine. As discussed above, a hydro-substituted halocarbon possesses a much lower atmospheric lifetime than fully halogenated chlorofluorocarbons. However, decreasing the halogen content of the carrier gas, by incorporating hydrogen in the molecule, tends to reduce the flammability suppressant or extinction properties of the carrier gas.

measuring the flame limits of vapors in air. The ASTM E-681 method involves preparing a gas phase mixture of ethylene oxide, carrier gas, and air in a 5-liter spherical vessel. Once the components have been adequately mixed, the gas mixture is ignited at the center of the vessel. If a flame propagates horizontally then the gas mixture is deemed flammable. The extent of flame propagation necessary for the mixture to be classified as flammable is defined in the ASTM E-681 method definition.

Gas mixtures were prepared by evacuating the vessel and admitting the carrier gas, ethylene oxide and air, measuring the pressure after each addition. The composition of the blend is determined from the component partial pressures. A uniform composition is ensured by stirring the mixture with a magnetically driven propeller. The ignition source employed to determine the flammability characteristics of the carrier gas/ethylene oxide blends consisted of a paper match head held in a coil of nichrome wire. Heating the wire electrically causes the match to ignite.

By preparing various compositions of ethylene oxide and carrier gas in air and determining their flammability, it is possible to map out the region of compositions in air which are flammable (see, for example, P. A. Sanders, *Principles of Aerosol Technology*, 146 (Van Nostrand Reinhold (1970)). The maximum amount of ethylene oxide which can be blended with the carrier gas, yet remain nonflammable in all proportions in air, can be determined from such a plot.

Flammability measurements were performed for ethylene oxide blends with a series of fluorinated ethanes (replace hydrogen with fluorine one by one). HFC-143a ($CF_3$—$CH_3$), HFC-134a ($CF_3$—$CH_2F$), HFC-125 ($CF_3$—$CHF_2$) and HFC-116 ($CF_3$—$CF_3$) in addition to HCFC-124 ($CHClF$—$CF_3$) and CFC-12 ($CCl_2F_2$). The HCFC's and HFC's are all regarded as environmentally acceptable materials. HFC-134a has been suggested as an alternative for CFC-12 in certain air conditioning and refrigeration applications. These fluorocarbons possess different properties than HFE-125 and are included for the sake of comparison. Table 1 summarizes the maximum or critical composition of ethylene oxide attainable with these materials as well as some molecular properties of the diluents.

TABLE 1

|  | CFC-12 $CCl_2F_2$ | HCFC-124 $CHClFCF_3$ | HFC-116 $CF_3CF_3$ | HCFC-125 $CF_3CHF_2$ | HFC-134a $CF_3CH_2F$ | HFC-143a $CF_3CH_3$ | HFE-125 $CF_3OCHF_2$ |
|---|---|---|---|---|---|---|---|
| Maximum ethylene oxide (vol %) | 22.6 | 24.6 | 18.9 | 23.7 | 16.3 | 0.0 | 21.8 |
| Halogen Content Of Diluents |  |  |  |  |  |  |  |
| Wt. % Chlorine | 58.6 | 26.1 | 0.0 | 0.0 | 0.0 | 0.0 | 0.0 |
| Wt. % Fluorine | 31.4 | 55.9 | 82.6 | 79.2 | 74.5 | 67.8 | 69.9 |
| Wt. % Halogen | 90.0 | 82 | 82.6 | 79.2 | 74.5 | 67.8 | 69.9 |
| Mole % Chlorine | 40.0 | 12.5 | 0.0 | 0.0 | 0.0 | 0.0 | 0.0 |
| Mole % Fluorine | 40.0 | 50 | 75.0 | 62.5 | 50.0 | 37.5 | 55.5 |
| Mole % Halogen | 80.0 | 62.5 | 75.0 | 62.5 | 50.0 | 37.5 | 55.5 |

EXAMPLE 1

This example shows by means of vapor phase flammability measurements for various ethylene oxide/carrier gas mixtures in air that HFE-125 surprisingly suppresses the flammability of ethylene oxide at least as well as CFC-12.

Flammability measurements were performed using a method based on the ASTM E-681 method prescribed for Based upon halogen content (wt %), one would expect the following pattern of flame suppressant behavior CFC-12 >CFC-116 >HCFC-124 >HFC-125 >HFC-134a >HFE-125 >HFC- 143 a. However, the data show that for this ignition source, surprisingly, an essentially equivalent amount of ethylene oxide is provided for sterilization by using the HFE-125 carrier gas as would be using HCFC-124 or CFC-12.

EXAMPLE 2

The experiment outlined in Example 1 was repeated using a spark ignition source.

Table 2 lists the critical ethylene oxide concentration as well as some of the physical and molecular properties of the fluorocarbon diluents.

TABLE 2

|  | CFC-12<br>$CCl_2F_2$ | HFC-116<br>$CF_3CF_3$ | HCFC-125<br>$CF_3CHF_2$ | HFC-134a<br>$CF_3CH_2F$ | HFC-143a<br>$CF_3CH_3$ | HFE-125<br>$CF_3OCHF_2$ |
|---|---|---|---|---|---|---|
| Maximum ethylene oxide (vol %) | 26.9 | 25.9 | 23 | 16 | 0.0 | 17.6 |
| Halogen Content Of Diluents |  |  |  |  |  |  |
| Wt. % Chlorine | 58.6 | 0.0 | 0.0 | 0.0 | 0.0 | 0.0 |
| Wt. % Fluorine | 31.4 | 82.6 | 79.2 | 74.5 | 67.8 | 69.9 |
| Wt. % Halogen | 90.0 | 82.6 | 79.2 | 74.5 | 67.8 | 69.9 |
| Mole % Chlorine | 40.0 | 0.0 | 0.0 | 0.0 | 0.0 | 0.0 |
| Mole % Fluorine | 40.0 | 75.0 | 62.5 | 50.0 | 37.5 | 55.5 |
| Mole % Halogen | 80.0 | 75.0 | 62.5 | 50.0 | 37.5 | 55.5 |

Although these data show that HFE-125 possesses flame suppressant properties which make it an acceptable diluent for ethylene oxide, they do not confirm the dramatic results of Example 1. After reviewing the conditions and materials used in the experiment, principally the ignition source, we discovered that the data reported in Example 2 were collected over a period of time in which the ignition source underwent significant change including inductance generation, ac transformer generation and spark duration lengthening. These changes would have affected the values obtained. As a result, a side by side comparison of the data generated in Examples 1 and 2 is not meaningful.

EXAMPLE 3

The vapor pressure of a commercial blend of CFC-12/ ethylene oxide (12/88 wt % ethylene oxide/CFC-12) and a 8.3/91.7 wt % blend of ethylene oxide/HFE-125 (critical flammability ratio) was estimated using Raoult's Law to be 75 psia and 95 psia, respectively. Nonflammable HFE-125/ ethylene oxide blends possess vapor pressures greater than 1 atmosphere (14.7 psia), which is sufficient to expel the liquid mixture from a source cylinder to the evacuated or partially evacuated sterilizer chamber.

EXAMPLE 4

The miscibility of ethylene oxide with HFE-125 was examined. An 11.31 wt % mixture of ethylene oxide in HFE-125 was prepared. We visually observed that the composition was a single liquid phase at room temperature and when submerged in dry ice pellets (−78° C.).

EXAMPLE 5

Compatibility tests are performed by exposing plastics and polymers commonly used in the construction of medical devices to HE-125 vapor at 24.7 psia and 130° C. for 16 hours. At the end of the exposure period the parts are visually inspected and any change in the weight of the part is determined. The materials that are studied include: polypropylene, polycarbonate (Lexan), polystyrene, polypropylene, latex/silicone rubber, PVC, cotton gauze and synthetic skin. The data indicate essentially no difference in compatibility properties between CFC-12 and HFE-125. Further, those plastics like polycarbonate and polystyrene which are incompatible with certain fluorocarbons show no deleterious effect when exposed to HFE-125.

What is claimed is:

1. Sterilizing gas compositions comprising about 6.5 to about 27 mole % ethylene oxide and a flame suppressing composition comprising pentafluorodimethyl ether.

2. The sterilizing gas compositions of claim 1 wherein said compositions comprise about 93.5 to about 73 mole percent of said flame suppressing composition.

3. The sterilizing gas compositions of claim 2 wherein said compositions comprise from about 17.2 to about 21.8 mole percent ethylene oxide and from about 82.8 to about 78.2 mole percent of said flame suppressing composition.

4. The sterilizing gas compositions of claim 3 wherein said compositions comprise about 17.3 mole percent ethylene oxide and about 82.7 mole percent of said flame suppressing composition.

5. The sterilizing gas compositions of claim 1 comprising from about 92.5 to about 1 mole percent of said flame suppressing composition, from about 6.5 to about 27 mole percent ethylene oxide and from about 1 to about 92.5 mole percent of a nonflammable, inert component which is more volatile than the pentafluorodimethyl ether/ethylene oxide blend and is capable of increasing the autogeneous pressure of the blend.

6. The sterilizing gas composition of claim 5 wherein said more volatile, non flammable inert component is selected from the group consisting of carbon dioxide, pentafluoroethane, trifluoromethane, carbon tetrafluoride, and hexafluoroethane.

7. The sterilizing gas composition of claim 6 wherein said more volatile, nonflammable inert component is pentafluoroethane.

8. The sterilizing gas composition of claim 6 wherein said more volatile, nonflammable inert component is carbon tetrafluoride.

9. The sterilizing gas composition of claim 6 wherein said more volatile, nonflammable inert component is hexafluoroethane.

10. The sterilizing gas compositions of claim 1 comprising from about 92.5 to about 1 mole percent of a flame suppressing composition comprising pentafluorodimethyl ether, from about 6.5 to about 27 mole percent ethylene oxide and from about 1 to about 92.5 mole percent of a nonflammable, inert component which is less volatile than the pentafluorodimethyl ether/ethylene oxide blend and is capable of decreasing the autogeneous pressure of the blend.

11. The sterilizing gas composition of claim 10 wherein said less volatile, non flammable inert component is selected from the group consisting of heptafluoropropane, octafluorocyclobutane, propylene oxide and tetrafluoroethane.

12. The sterilizing gas composition of claim 11 wherein said less volatile, nonflammable inert component is heptafluoropropane.

13. The sterilizing gas composition of claim 11 wherein said less volatile, nonflammable inert component is octafluorocyclobutane.

14. The sterilizing gas composition of claim 11 wherein said less volatile, nonflammable inert component is tetrafluoroethane.

15. A method of sterilizing articles comprising exposing said articles to a sterilizing gas composition of claim 1 under conditions and for a period of time necessary to achieve the desired degree of sterility.

16. A method of sterilizing articles comprising exposing said articles to a sterilizing gas composition of claim 2 under conditions and for a period of time necessary to achieve the desired degree of sterility.

17. A method of sterilizing articles comprising exposing said articles to a sterilizing gas composition of claim 3 under conditions and for a period of time necessary to achieve the desired degree of sterility.

18. A method of sterilizing articles comprising exposing said articles to a sterilizing gas composition of claim 4 under conditions and for a period of time necessary to achieve the desired degree of sterility.

19. A method of sterilizing articles comprising exposing said articles to a sterilizing gas composition of claim 5 under conditions and for a period of time necessary to achieve the desired degree of sterility.

20. A method of sterilizing articles comprising exposing said articles to a sterilizing gas composition of claim 10 under conditions and for a period of time necessary to achieve the desired degree of sterility.

* * * * *